(12) United States Patent
Hiei et al.

(10) Patent No.: US 10,588,559 B2
(45) Date of Patent: Mar. 17, 2020

(54) AIR-CONDITIONING CONTROL SYSTEM

(71) Applicant: DAIKIN INDUSTRIES, LTD., Osaka-shi, Osaka (JP)

(72) Inventors: Takehiko Hiei, Osaka (JP); Kazuhisa Shigemori, Osaka (JP); Sayo Toramoto, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 88 days.

(21) Appl. No.: 15/746,909

(22) PCT Filed: Jun. 3, 2016

(86) PCT No.: PCT/JP2016/002694
§ 371 (c)(1),
(2) Date: Jan. 23, 2018

(87) PCT Pub. No.: WO2017/022157
PCT Pub. Date: Feb. 9, 2017

(65) Prior Publication Data
US 2019/0137136 A1    May 9, 2019

(30) Foreign Application Priority Data

Jul. 31, 2015   (JP) ................................ 2015-152253

(51) Int. Cl.
*A61B 5/16*   (2006.01)
*F24F 11/89*  (2018.01)
(Continued)

(52) U.S. Cl.
CPC ............ *A61B 5/16* (2013.01); *A61B 5/02405* (2013.01); *A61B 5/1102* (2013.01);
(Continued)

(58) Field of Classification Search
CPC ............................ G01N 33/0075; G08B 21/22
See application file for complete search history.

(56) References Cited

U.S. PATENT DOCUMENTS 7,580,745 B2 *  8/2009  Pastore .............. A61B 5/02405
                                                          607/17
9,420,383 B1 *  8/2016  Lee ...................... H04R 25/554
(Continued)

FOREIGN PATENT DOCUMENTS

CN    103824436 A    5/2014
JP    2003-38630 A   2/2003
(Continued)

OTHER PUBLICATIONS

International Search Report for PCT/JP2016/002694 (PCT/ISA/210) dated Aug. 23, 2016.

*Primary Examiner* — Santosh R Poudel
(74) *Attorney, Agent, or Firm* — Birch, Stewart, Kolasch & Birch, LLP

(57) ABSTRACT

An air-conditioning control system provides an appropriate environment in accordance with a stress level of a person in a room and a use of a space in which the person stays. A deriver derives heartbeat-related parameters based on a body movement of the person. A determiner determines a stress level of the person at a current moment, based on the heartbeat-related parameters. A receiver receives a use of the space for the person. A CPU for appliance control (i) selects a heartbeat-related parameter to be changed, depending on the received use and the heartbeat-related parameters, and (ii) controls operation of the air conditioner to change the selected heartbeat-related parameter to be changed.

6 Claims, 8 Drawing Sheets

PRIORITIES OF HEARTBEAT-RELATED PARAMETERS

| PRIORITY | USE INFORMATION ITEM | | | 45 |
|---|---|---|---|---|
| | TO FOCUS | TO FEEL RELAXED | TO FEEL REFRESHED | |
| 1 | LF/HF | HF | SDNN | |
| 2 | HF | SDNN | HF | |
| 3 | SDNN | | | |

(51) Int. Cl.
  *A61B 5/00* (2006.01)
  *A61B 5/024* (2006.01)
  *A61B 5/11* (2006.01)
  *F24F 11/80* (2018.01)
  *F24F 11/63* (2018.01)
  *F24F 120/20* (2018.01)
  *F24F 120/14* (2018.01)

(52) U.S. Cl.
  CPC .......... *A61B 5/4836* (2013.01); *A61B 5/6891* (2013.01); *F24F 11/63* (2018.01); *F24F 11/80* (2018.01); *F24F 11/89* (2018.01); *A61B 5/165* (2013.01); *F24F 2120/14* (2018.01); *F24F 2120/20* (2018.01); *F24F 2221/02* (2013.01)

(56) References Cited

U.S. PATENT DOCUMENTS

| | | | |
|---|---|---|---|
| 9,675,258 B2* | 6/2017 | Stergiou | A61B 5/02405 |
| 2007/0032733 A1* | 2/2007 | Burton | A61B 5/02405 |
| | | | 600/509 |
| 2010/0125217 A1* | 5/2010 | Kuo | A61B 5/02405 |
| | | | 600/515 |
| 2010/0234747 A1 | 9/2010 | Hatakeyama | |
| 2012/0149973 A1* | 6/2012 | Holloway | A61N 1/36025 |
| | | | 600/28 |
| 2014/0207292 A1* | 7/2014 | Ramagem | G05B 15/02 |
| | | | 700/278 |
| 2014/0310186 A1* | 10/2014 | Ricci | H04W 4/21 |
| | | | 705/302 |
| 2015/0158425 A1* | 6/2015 | Han | B60Q 9/00 |
| | | | 701/41 |
| 2015/0217082 A1* | 8/2015 | Kang | G16H 50/30 |
| | | | 600/28 |
| 2016/0339300 A1* | 11/2016 | Todasco | H04W 4/80 |
| 2016/0374606 A1* | 12/2016 | Shikii | A61B 5/18 |
| | | | 600/301 |
| 2018/0125418 A1* | 5/2018 | Haakma | A61B 5/0205 |
| 2018/0220957 A1* | 8/2018 | Fuerst | A61B 5/486 |
| 2018/0321700 A1* | 11/2018 | Kwak | G05D 23/19 |

FOREIGN PATENT DOCUMENTS

| | | |
|---|---|---|
| JP | 2003-42509 A | 2/2003 |
| JP | 2006-320621 A | 11/2006 |
| JP | 2009-39167 A | 2/2009 |
| JP | 2015-108469 A | 6/2015 |

* cited by examiner

FIG.4

STRESS LEVEL DETERMINATION TABLE 26

| LF/HF AUTONOMIC BALANCE | HF INDEX OF PARASYMPATHETIC NERVE | SDNN AUTONOMIC NEURAL ACTIVITY | STRESS LEVEL |
|---|---|---|---|
| HIGH<br>• SYMPATHETIC NERVE IS MORE ACTIVE<br>• "OUT OF" AUTONOMIC BALANCE | HIGH<br>(RELAXED) | HIGH<br>(AUTONOMIC NEURAL IS ACTIVE) | LEVEL A |
| | | LOW<br>(AUTONOMIC NEURAL IS NOT ACTIVE) | LEVEL B |
| | LOW<br>(NOT RELAXED) | HIGH<br>(AUTONOMIC NEURAL IS ACTIVE) | LEVEL C |
| | | LOW<br>(AUTONOMIC NEURAL IS NOT ACTIVE) | LEVEL D |
| LOW<br>• PARASYMPATHETIC NERVE IS MORE ACTIVE<br>• "IN" AUTONOMIC BALANCE | HIGH<br>(RELAXED) | HIGH<br>(AUTONOMIC NEURAL IS ACTIVE) | LEVEL E |
| | | LOW<br>(AUTONOMIC NEURAL IS NOT ACTIVE) | LEVEL F |
| | LOW<br>(NOT RELAXED) | HIGH<br>(AUTONOMIC NEURAL IS ACTIVE) | LEVEL G |
| | | LOW<br>(AUTONOMIC NEURAL IS NOT ACTIVE) | LEVEL H |

FIG.7

PARAMETER SELECTION TABLE

| | USE INFORMATION ITEM | | |
|---|---|---|---|
| STRESS LEVEL | TO FOCUS | TO FEEL RELAXED | TO FEEL REFRESHED |
| LEVEL A | LF/HF | HF | SDNN |
| LEVEL B | SDNN | SDNN | SDNN |
| LEVEL C | HF | HF | HF |
| LEVEL D | HF | HF | SDNN |
| LEVEL E | LF/HF | HF | SDNN |
| LEVEL F | LF/HF | SDNN | SDNN |
| LEVEL G | LF/HF | HF | HF |
| LEVEL H | LF/HF | HF | SDNN |

PRIORITIES OF HEARTBEAT-RELATED PARAMETERS

| | USE INFORMATION ITEM | | |
|---|---|---|---|
| PRIORITY | TO FOCUS | TO FEEL RELAXED | TO FEEL REFRESHED |
| 1 | LF/HF | HF | SDNN |
| 2 | HF | SDNN | HF |
| 3 | SDNN | | |

APPLIANCE CONTROL TABLE 46

| SEASON | PARAMETER TO BE RAISED | SET TEMPERATURE OF AIR CONDITIONER | ILLUMINANCE OF LIGHTING APPLIANCE | OUTPUT FROM ACOUSTIC APPLIANCE | AROMA FROM AROMA GENERATION APPLIANCE |
|---|---|---|---|---|---|
| ... | ... | ... | ... | ... | ... |
| SUMMER | LH/HF | 25°C | WHITISH COLOR 6000k, 750lx | SOUND OF RAIN | MINT |
| | HF | 27°C | WARM COLOR 4000k, 400lx | SOUND OF RUSHING CREAK | LAVENDER |
| | SDNN | 28°C | WARM COLOR 3000k, 200lx | 90BPM,FOUR-FOUR, PIANO AND STRING INSTRUMENT | HINOKITIOL |
| ... | ... | ... | ... | ... | ... |
| WINTER | LH/HF | 20°C | WHITISH COLOR 6000k, 750lx | SOUND OF RAIN | MINT |
| | HF | 21°C | WARM COLOR 4000k, 400lx | SOUND OF RUSHING CREAK | LAVENDER |
| | SDNN | 22°C | WARM COLOR 3000k, 200lx | 90BPM,FOUR-FOUR, PIANO AND STRING INSTRUMENT | HINOKITIOL |

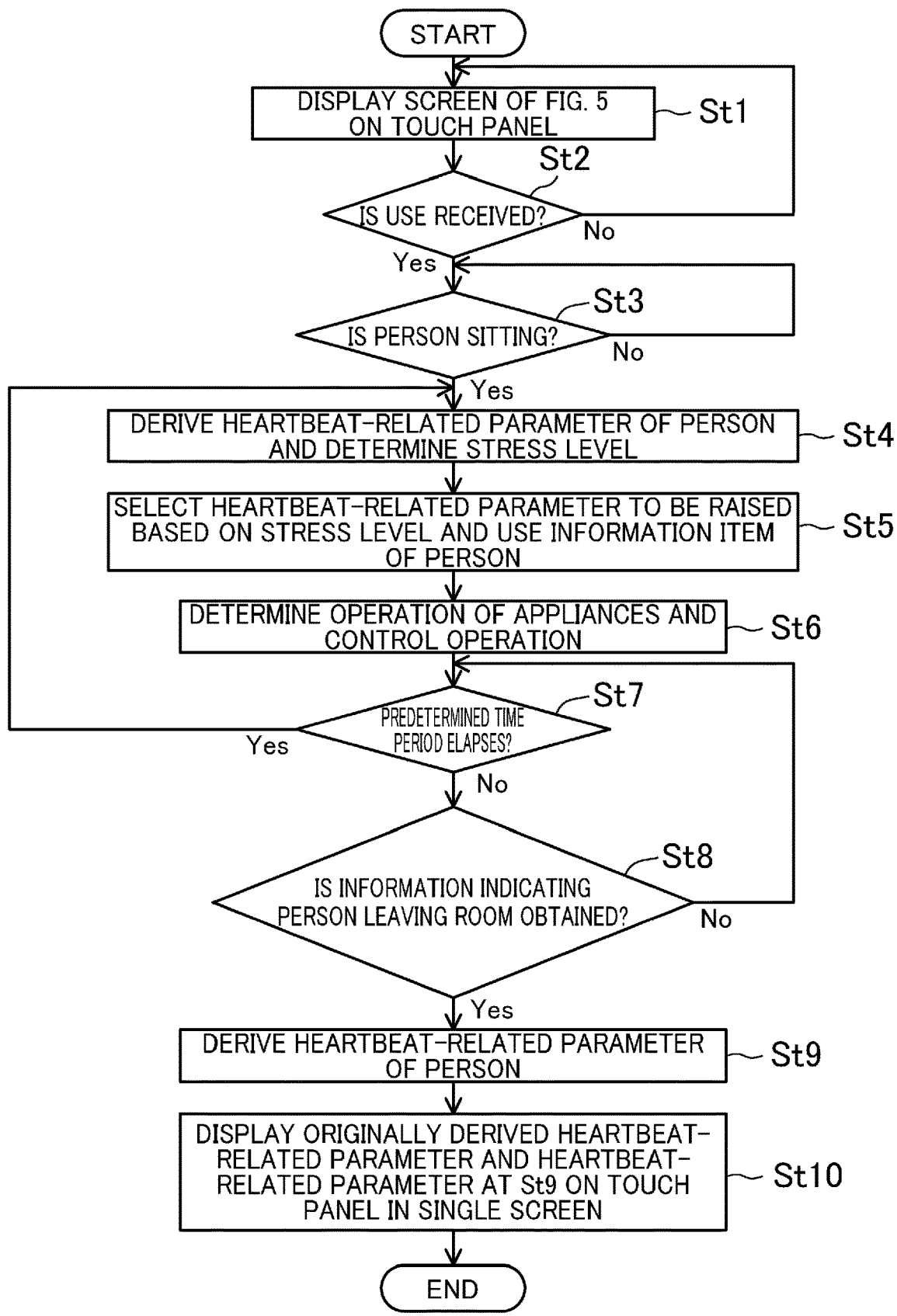

AIR-CONDITIONING CONTROL SYSTEM

TECHNICAL FIELD

The present invention relates to a system to control an air conditioner.

BACKGROUND ART

A service in recent years offers a space to change a stress level of a person in a room. As a technique for such a service, for example, a system according to Patent Document 1 is known. Upon determination of a stress level (e.g., a strain level and a fatigue level) of a person in a room, the system in Patent Document 1 automatically generates stimuli based on a result of the determination to give the person such effects as easing strain and reducing fatigue. Examples of the stimuli include refreshing sound, color, and aroma. The stimuli reduce the strain level and the fatigue level of the person.

CITATION LIST

Patent Documents

[Patent Document 1] Japanese Unexamined Patent Publication No. 2006-320621

SUMMARY OF THE INVENTION

Technical Problem

In the Patent Document 1, the stimuli such as sound and aroma are automatically selected and output to the person in the room to make the person feel relaxed if the determination result shows that the person is in a strained state, and to make the person feel refreshed if the determination result shows that the person is in a fatigued state.

However, some strained people in the room would rather maintain their focus to make progress on their tasks than feel refreshed. Hence, uses of the space might be different depending on the people. Whereas, the system in Patent Document 1 automatically operates to make a person in a room feel refreshed. Hence, even though the person is in a strained state and desires to maintain his or her focus, the system in Patent Document 1 ignores the intension of the person and automatically leads the person from the strained state to a relaxed state. As a result, work efficiency of the person declines.

The present invention is conceived in view of the above problems, and intends to offer an appropriate environment depending on a stress level of, and a use of a space for, a person in a room.

Solution to the Problem

A first aspect of the present disclosure is directed to an air-conditioning control system. The air-conditioning control system includes: a measurer (21, 23) measuring a body movement of a person (E) in a room a space (S) of which is to be air-conditioned by an air conditioner (A); a deriver (27a) deriving heartbeat-related parameters based on a result of the measurement by the measurer (21, 23), the heartbeat-related parameters being related to N-N intervals of the person (E); a determiner (27b) determining a stress level of the person (E) at a current moment, based on the heartbeat-related parameters; a receiver (41) capable of receiving a use information item indicating a use of the space (S) for the person (E); and an operation controller (48) (i) selecting a heartbeat-related parameter to be changed from among the heartbeat-related parameters depending on the result of the determination by the determiner (27b) and the use information item, and (ii) controlling operation of the air conditioner (A) to change the selected heartbeat-related parameter to be changed.

Here, the operation of the air conditioner (A) is not controlled to simply change the heart-rate-related parameter of the person (E). The operation of the air conditioner (A) is controlled to change the heart-rate-related parameter, depending on a use of the space (S) for the person (E). For example, the use for the person (E) is "TO FOCUS." In this case, if the person (E) has already been in the strained state, the environment control system (10) operates the air conditioner (A) so that the strained state of the person (E) continues longer, instead of making the person (E) feel relaxed. Moreover, if the person (E) is in the fatigued state, the air-conditioning control system (10) causes the air conditioner (A) to operate so that the person (E) is guided to feel strained, instead of being guided to feel relaxed. Hence, the air-conditioning control system (10) provides the space (S) with an environment for guiding the person (E) to a stress level which conforms to a use of the space (S). Thus, the person (E) can change or maintain his or her stress level, and efficiently use, the space (S) depending on the use of the space (S).

In a second aspect directed to the air-conditioning control system of the first aspect, the heartbeat-related parameters may have priorities previously set for each of use information items, and the operation controller (48) may select the heartbeat-related parameter to be changed, depending on the priorities corresponding to the received use information item, and the result of the determination by the determiner (27b).

The heartbeat-related parameter to be changed is selected not at random but as appropriate to suit the use for the person (E). Thus, the stress level of the person (E) can be adjusted to suit the use more exactly so that the person (E) can easily achieve the purpose of the use.

In a third aspect directed to the air-conditioning control system of the second aspect, the air-conditioning control system may further include a storage unit (43) storing parameter selection information (44) including the heartbeat-related parameter to be changed in association with each of the use information items and stress levels, wherein the determiner (27b) may compare the heartbeat-related parameters with thresholds each corresponding to one of the heartbeat-related parameters to determine the stress level of the person (E), in the parameter selection information (44), the heartbeat-related parameter to be changed may be determined in accordance with the priorities for each of the use information items and a magnitude relationship between the heartbeat-related parameters and the corresponding thresholds, and the operation controller (48) may select the heartbeat-related parameter to be selected, using the parameter selection information (44).

Using the parameter selection information (44), the operation controller (48) can easily and quickly determine a heartbeat-related parameter to be changed for achieving the purpose of use for the person (E), without determining the priorities every time. Such a feature facilitates processing for selection of the heartbeat-related parameter, reducing the time period required for the processing.

In the fourth aspect directed to the air-conditioning control system of the second aspect or the third aspect, if the person (E) is in the stress level in which: the heartbeat-related parameters below the thresholds are not found, the operation controller (48) may cause the air conditioner (A) to raise a heartbeat-related parameter included in the heartbeat-related parameters and having a highest priority among the priorities; one of the heartbeat-related parameters is below a corresponding one of the thresholds, the operation controller (48) may cause the air conditioner (A) to raise either the one heartbeat-related parameter or the heartbeat-related parameter having the highest priority; and two or more of the heartbeat-related parameters are below respective thresholds among the thresholds, the operation controller (48) may cause the air conditioner (A) to raise the heartbeat-related parameter having the highest priority.

(I) If the person (E) is in a stress level in which the heartbeat-related parameters below the thresholds are not found, the environment control system (10) causes the air conditioner (A) to raise the heartbeat-related parameter having the highest priority. Hence the current heart-rate-related parameter is maintained. If the person (E) is in a stress level in which one of the heartbeat-related parameters is below a corresponding one of the thresholds, and the one heartbeat-related parameter below the threshold is raised, the parameter is needed to achieve the purpose of use. Hence, the air conditioner (A) operates to raise the one heart-rate-related parameter. Moreover, if the person (E) is in a stress level in which one of the heartbeat-related parameters is below the corresponding threshold and the one heartbeat-related parameter below the threshold is not related to the use, the air conditioner (A) operates to raise the heartbeat-related parameter having the highest priority. If the person (E) is in a stress level in which two or more of the heartbeat-related parameters are below respective thresholds, the air conditioner (A) operates to raise the heartbeat-related parameter having the highest priority for achieving the purpose of use. Hence, the air-conditioning control system (10) can reliably select a heartbeat-related parameter to be raised, depending on the presence or absence of a heartbeat-related parameter below the corresponding threshold and the number of heartbeat-related parameters below respective thresholds, contributing to providing an environment in which a stress level of the person (E) conforms to a use of the space (S).

In a fifth aspect directed to the air-conditioning control system of any one of the second to fourth aspects, the heartbeat-related parameters may include a standard deviation of N-N intervals (SDNN) of the person (E), a ratio of a low frequency component to a high frequency component (LF/HF) in a variation of the N-N intervals, and a high frequency component (HF) in the variation of the N-N intervals, and if the use information item indicates maintenance of or improvement in a focused state of the person (E), the priorities may be set in an order of the ratio of the low frequency component to the high frequency component (LF/HF) in the variation of the N-N intervals, the high frequency component (HF) in the variation of the N-N intervals, and the standard deviation of the N-N intervals (SDNN).

Such a feature makes the space (S) appropriate for the use; namely, maintaining or improving the focused state of the person (E).

In a sixth aspect directed to the air-conditioning control system of any one of the first to fifth aspects, the measurer (21, 23) may measure a body movement of the person (E) during the operation of the air conditioner (A), the deriver (27a) may derive the heartbeat-related parameters of the person (E) during the operation of the air conditioner (A), the determiner (27b) may determine the stress level of the person (E) during the operation of the air conditioner (A), and the operation controller (48) may reselect the heartbeat-related parameter to be changed depending on the stress level of the person (E) during the operation of the air conditioner (A) and the use information item, and feedback-controls the operation of the air conditioner (A) so that the reselected heartbeat-related parameter changes.

Such a feature allows the environment control system (10) to provide the space (S) with an environment which precisely suits stress levels of the person (E) at different times.

In a seventh aspect directed to the air-conditioning control system of any one of the first to sixth aspects, the measurement by the measurer (21,23), the derivation by the deriver (27a), and the determination by the determiner (27b) may be carried out at least before and after the air conditioner (A) starts the operation corresponding to the use information item, and the air-conditioning control system may further include an annunciator (41) announcing to the person (E) the stress level before and after the air conditioner (A) starts the operation corresponding to the use information item.

Such a feature allows the person (E) to identify how much the heartbeat-related parameter of the person (E) himself or herself has changed before and after the start of the operation of the air conditioner (A) for the use.

In an eighth aspect directed to the air-conditioning control system of any one of the first to seventh aspects, the air-conditioning control system may further include at least one of a lighting appliance (B), an acoustic appliance (C), and an aroma generation appliance (D) all of which correspond to the space (S), wherein the operation controller (48) may further control operation of at least one of the lighting appliance (B), the acoustic appliance (C), and the aroma generation appliance (D) so that the selected heartbeat-related parameter is changed.

Such a feature allows the air-conditioning control system (10) to provide an environment in which the heartbeat-related parameter changes more easily in conformity with a use for the person (E) than when the air conditioner (A) alone operates.

Advantages of the Invention

Thanks to the first aspect of the present disclosure, the person (E) can change or maintain his or her stress level, and efficiently use the space (S) depending on the use of the space (S).

Thanks to the second aspect, the stress level of the person (E) can be adjusted to suit the use more exactly so that the person (E) can easily achieve the purpose of the use.

Thanks to the third aspect, processing for selection of the heartbeat-related parameter is facilitated, reducing the time period required for the processing.

Thanks to the fourth aspect, a heartbeat-related parameter to be raised can be reliably selected, depending on the presence or absence of a heartbeat-related parameter below the corresponding threshold and the number of heartbeat-related parameters below respective thresholds. Such a feature contributes to providing an environment in which a stress level of the person (E) conforms to a use of the space (S).

Thanks to the fifth aspect, the space (S) is appropriate for the use; namely, maintaining or improving the focused state of the person (E).

Thanks to the sixth aspect, the space (S) becomes an environment which precisely suits stress levels of the person (E) at different times.

Thanks to the seventh aspect, the person (E) can identify how much the heartbeat-related parameter of the person (E) himself or herself has changed before and after the start of the operation of the air conditioner (A) for the use.

Thanks to the eighth aspect, the provided environment allows the heartbeat-related parameter to change more easily in conformity with a use for the person (E) than when the air conditioner (A) alone operates.

BRIEF DESCRIPTION OF THE DRAWINGS

FIG. 4 is a schematic view of a stress level determination table.

FIG. 7 is a schematic view of a parameter selection table.

FIG. 8 is a table for explaining a concept of priorities in the heartbeat-related parameters.

FIG. 9 is a schematic view of an appliance control table.

FIG. 10 is a flowchart showing a sequence of operation performed by the environment control system.

DETAILED DESCRIPTION

An embodiment of the present invention will now be described in detail with reference to the drawings. The embodiment below is merely an exemplary one in nature, and is not intended to limit the scope, applications, or use of the invention.

Embodiment

<Outline>
An environment control system (10) (equivalent to an air-conditioning control system) according to this embodiment determines a stress level of a person (E) in a room a space (S) of which is to be air-conditioned, and, depending on the stress level, at least controls an air conditioner (A) capable of influencing an environment of the space (S). In particular, the environment control system (10) controls operation of the air conditioner (A) so that the stress level of the person (E) conforms to a use of the space (S) for the person (E).

Other than the air conditioner (A), the environment control system (10) can control operation of a lighting appliance (B), a speaker (C) (equivalent to an acoustic appliance) to output sound at the person (E), and an aroma generation appliance (D) to generate aroma. Here, the lighting appliance (B) and the speaker (C) are in the space (S).

Here, an arrangement of various appliances (A to D) and furniture in the space (S) is described with reference to FIG. 1. In this embodiment, the space (S) is for example a private room in such a building as an office and an ordinary house.

One each of the air conditioner (A), lighting appliance (B), speaker (C), and aroma generation appliance (D) are installed for the space (S).

The air conditioner (A) and the aroma generation appliance (D) are placed on a floor in a space located across a sidewall (S1) from the space (S). The air conditioner (A) and the aroma generation appliance (D) are respectively connected to an air outlet (S1a) and an aroma injection hole (Sib) both formed on the sidewall (S1) of the space (S). The air conditioner (A) supplies conditioned air into the space (S) from the air outlet (S1a). The aroma generation appliance (D) supplies generated aroma into the space (S) from the injection hole (S1b).

The lighting appliance (B) and the speaker (C) are spaced apart from each other on a ceiling (S2) of the space (S). The lighting appliance (B), capable of changing the illuminance in multiple levels, includes multiple light-emitting diodes (LEDs), for example. The speaker (C) can switch between such sounds as various music tunes and sounds in nature, and output the sounds.

Moreover, in the space (S), a desk (F) for the person (E) to work with and a chair (G) for the desk (F) are provided. A personal computer (P) is placed on the desk (F).

Figure 1:
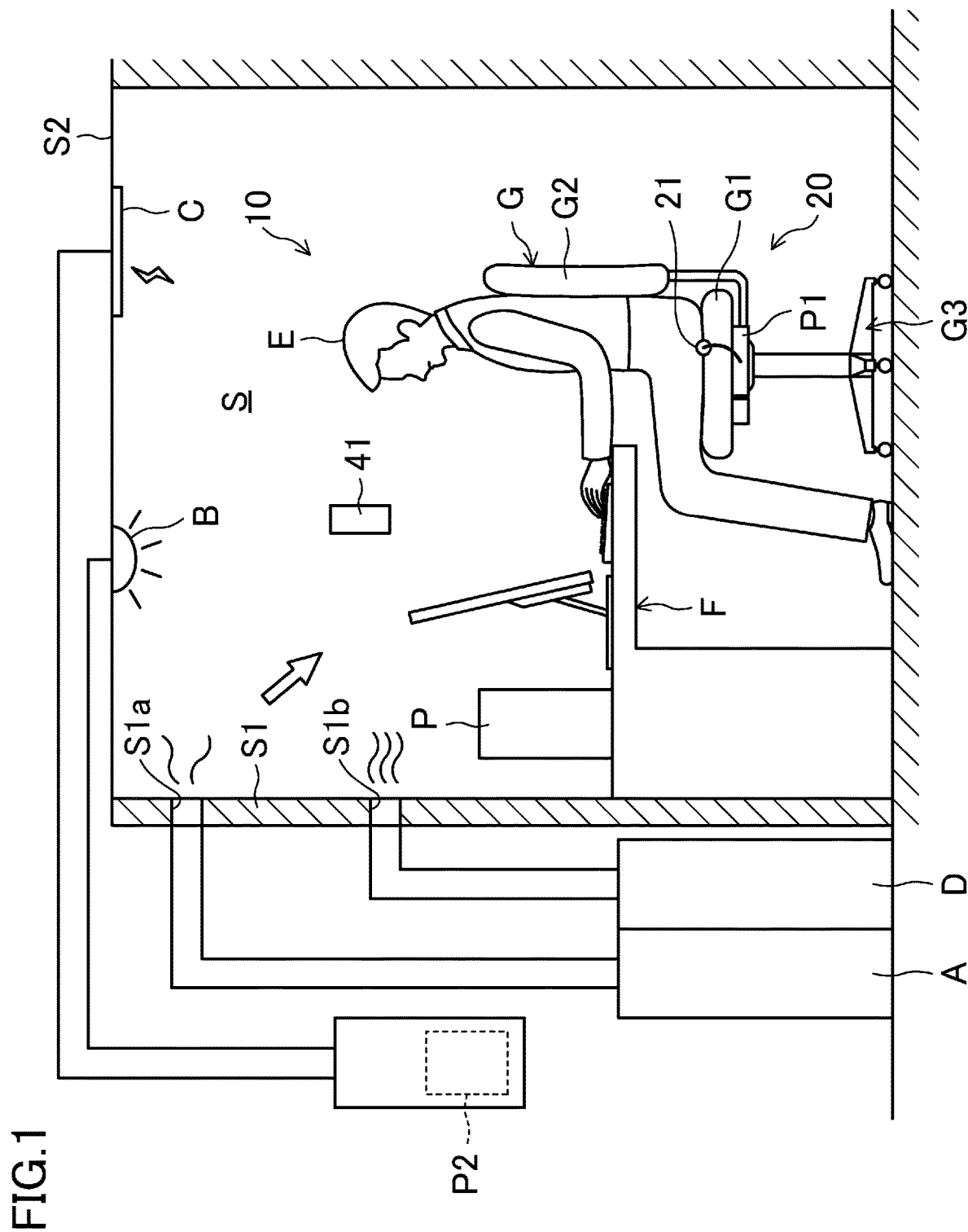
FIG. 1 is a schematic view illustrating a configuration of an environment control system according to this embodiment.
Figure 2:
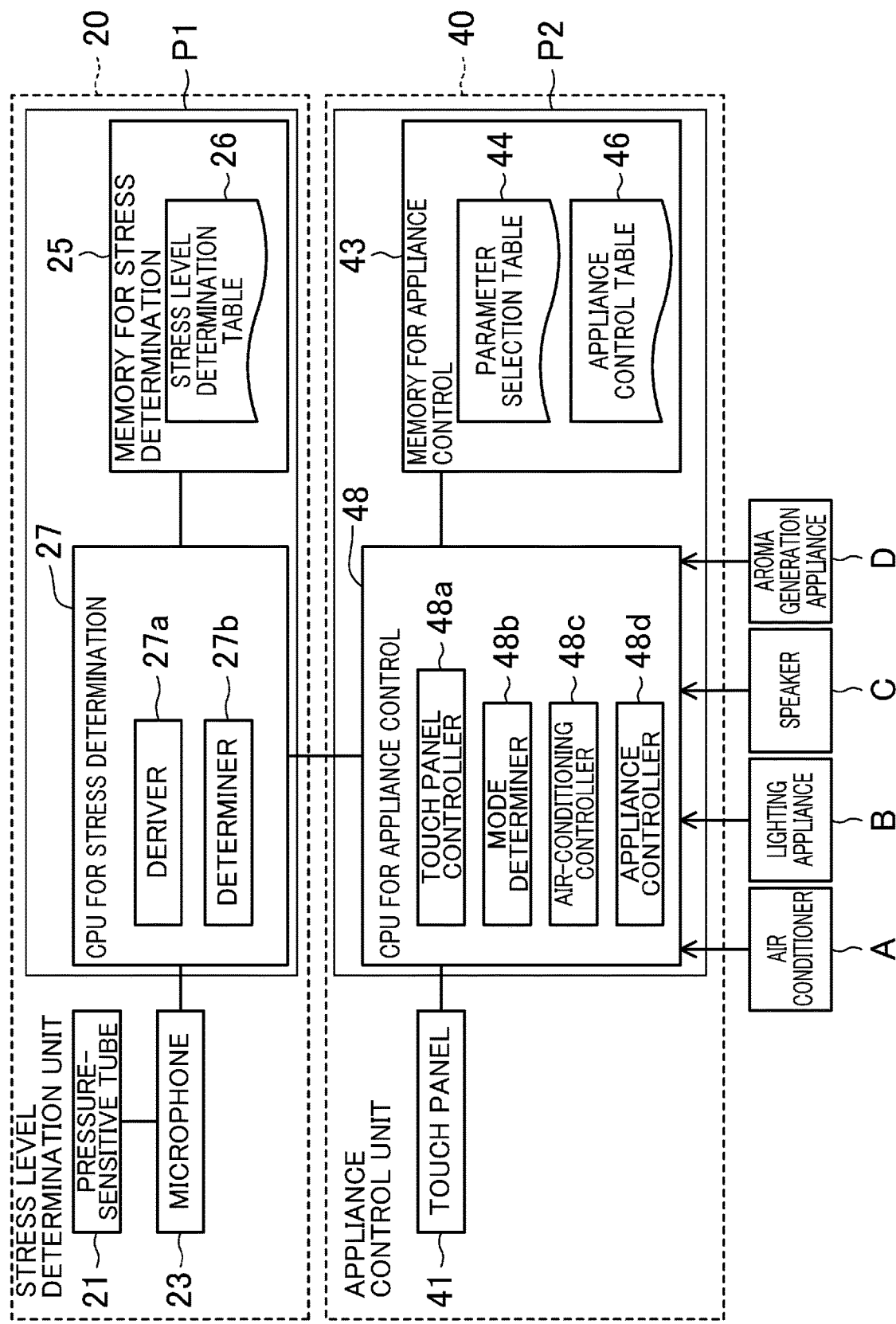
FIG. 2 is a block diagram schematically illustrating the configuration of the environment control system.

<Configuration of Environment Control System>
As illustrated in FIGS. 1 and 2, the environment control system (10) mainly includes a stress level determination unit (20) and an appliance control unit (40). The stress level determination unit (20) is secured mainly to the chair (G) on which the person (E) sits. The appliance control unit (40) is provided across the interior and the vicinity of the space (S). The stress level determination unit (20) and the appliance control unit (40) are communicably connected to each other.

Figure 3:
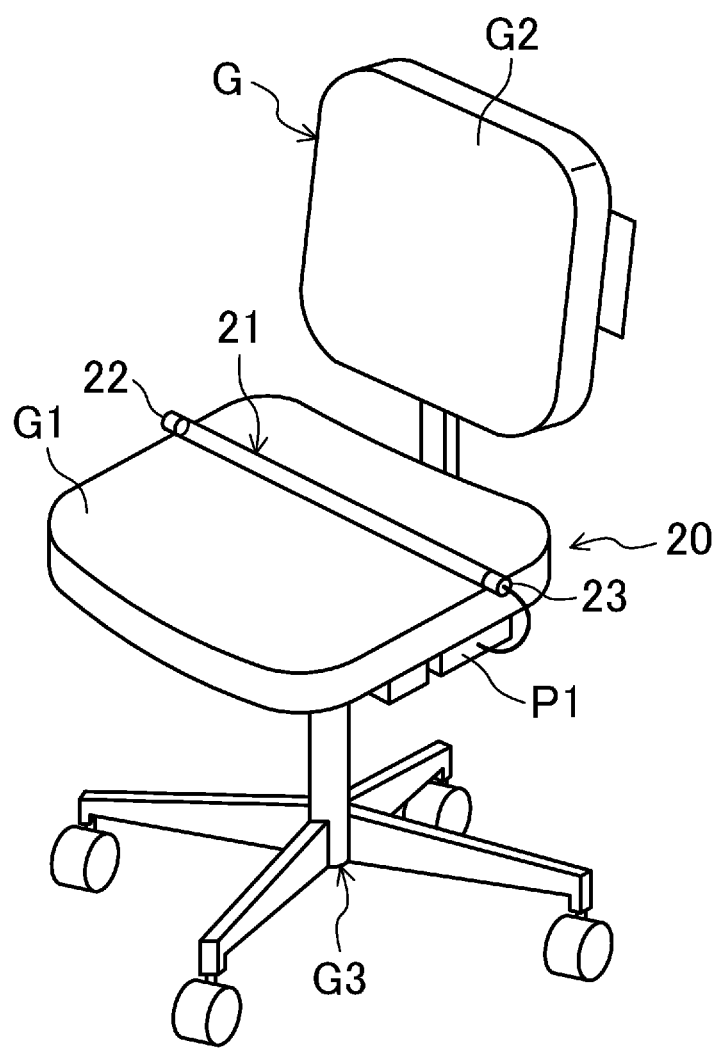
FIG. 3 is an external view of a chair with a stress level determination unit secured to the chair.

—Stress Level Determination Unit—
The stress level determination unit (20) obtains a stress level of the person (E) based on a current body movement of the person (E). As illustrated mainly in FIG. 2, the stress level determination unit (20) includes: a pressure-sensitive tube (21); a microphone (23); a memory for stress determination (25); and a central processing unit (CPU) for stress determination (27). As illustrated in FIGS. 1 and 3, the pressure-sensitive tube (21) and the microphone (23) are provided to a seat (G1) of the chair (G). As illustrated in FIG. 2, the memory for stress determination (25) and the CPU for stress determination (27) are mounted on a single printed board (P1). As illustrated in FIGS. 1 and 3, the printed board (P1) is provided to a rear face of the seat (G1); that is, toward a leg (G3) supporting the seat (G1). Moreover, the seat (G1) is provided with a battery (not shown) to be used as a power supply of the stress level determination unit (20).

Note that the printed board (P1) and the battery may be secured not to the seat (G1) but to a back (G2).

The pressure-sensitive tube (21) and the microphone (23) described below correspond to a "measurer" measuring the body movement of the person (E) in the space (S).

—Pressure-Sensitive Tube—
The pressure-sensitive tube (21) is made of such a resin material as polyvinyl chloride (PVC) and silicone, and shaped into a cylinder. In this embodiment, as an example, the pressure-sensitive tube (21) is provided toward the rear of the seat (G1) with respect to the center in a front-to-back direction, and linearly extends in a right-to-left direction (the right-to-left direction in FIG. 3). Specifically, the pressure-sensitive tube (21) is provided for the hip and the thighs of the person (E) when the person (E) sits on the chair (G).

A seal (22) is inserted into an opening on an end (the left end in FIG. 3) of the pressure-sensitive tube (21). The seal (22) blocks the end of the pressure-sensitive tube (21). The microphone (23) is inserted into an opening on another end (the right end in FIG. 3) of the pressure-sensitive tube (21). The microphone (23) blocks the other end of the pressure-sensitive tube (21).

Specifically, the pressure-sensitive tube (21) is hollow and tightly sealed.

—Microphone—

The microphone (23) is connected to an end of the pressure-sensitive tube (21). The microphone (23) acts as a pressure receiver (a pressure sensor) receiving an internal pressure of the pressure-sensitive tube (21).

Specifically, when the person (E) sits on the seat (G1), the internal pressure of the pressure-sensitive tube (21) changes with the change in body movement of the person (E). This change in internal pressure is received by the microphone (23). The microphone (23) lets a signal generated in accordance with a level of the pressure pass through a not-shown filter, and then outputs the signal to the CPU for stress determination (27).

—Memory for Stress Determination—

The memory for stress determination (25) includes such a semiconductor memory as a flash memory, and such a recording medium as a hard disc. The memory for stress determination (25) stores a stress level determination table (26), other than various programs to be read by the CPU for stress determination (27) so that the CPU for stress determination (27) executes various functions described below.

—Stress Level Determination Table—

Described here is the stress level determination table (26) with reference to FIG. 4. The stress level determination table (26) is used when the CPU for stress determination (27) determines a stress level of the person (E). The stress level determination table (26) is previously stored in the memory for stress determination (25) before the environment control system (10) is installed.

As illustrated in FIG. 4, the stress level determination table (26) includes factors associated with one another such as: autonomic balance "LF/HF"; index of parasympathetic nerve "HF"; autonomic neural activity "SDNN"; and stress level. All of the autonomic balance "LF/HF", the index of parasympathetic nerve "HF", and the autonomic neural activity "SDNN" are parameters for heartbeat intervals (hereinafter referred to as heartbeat-related parameters). The heartbeat-related parameters are particularly preferable to determine a stress level of the person (E) at a current moment.

The autonomic balance "LF/HF" indicates as an index a balance between the sympathetic nerve and the parasympathetic nerve of the person (E). Either the "HF" or the "LF" corresponds to one of two peaks obtained when a frequency analysis is performed on the heartbeat intervals described later. Specifically, the "HF" denotes a high frequency component (e.g., 0.20 Hz or higher), and the "LF" denotes a low frequency component (e.g., ranging from 0.05 Hz to 0.20 Hz). The "HF" appears when the parasympathetic nerve is more active than the sympathetic nerve (i.e., when the parasympathetic nerve is activated). The "LF" appears when either one of the sympathetic nerve or the parasympathetic nerve is more active than the other (i.e., when either one of the sympathetic nerve or the parasympathetic nerve is activated). Hence, the more the person (E) is in an excessively stressed state in which the sympathetic nerve is active, the higher the value of the autonomic balance "LF/HF" is. This shows that the person (E) is out of the autonomic balance. In contrast, the parasympathetic nerve is more active when the person (E) is in a relaxed state than in an excessively stressed state. Thus, the value of the autonomic balance "LF/HF" is lower in the relaxed state than in the excessively stressed state. This shows that the person (E) is in the autonomic balance.

Similar to the autonomic balance "LF/HF", the index of the parasympathetic nerve "HF", and the autonomic neural activity "SDNN" are obtained from heartbeat intervals.

As described above, the index of the parasympathetic nerve "HF" is lower as the person (E) is more excessively stressed, and, in contrast, higher as the person (E) is more relaxed.

The autonomic neural activity "SDNN" indicates a result of a standard deviation of N-N intervals; that is, a variability of heartbeat intervals. The more properly an autonomic nerve functions, the more clearly a variation synchronizing with breathing and blood pressure appears as a variation of heartbeat intervals. If the autonomic nerve is not functioning properly due to such effects as medication, the variation of heartbeat intervals is less likely to appear. Hence, a value of the autonomic neural activity "SDNN" is higher as the standard deviation of N-N intervals is larger, indicating that the autonomic nerve is active. In contrast, the value of the autonomic neural activity "SDNN" is lower as the standard deviation of N-N intervals is smaller, indicating that the autonomic nerve is not active.

FIG. 4 shows all the combinations of the heartbeat-related parameters when each of the heartbeat-related parameters; namely the autonomic balance "LF/HF", the index of the parasympathetic nerve "HF", and the autonomic neural activity "SDNN", is either "HIGH" or "LOW". In addition, FIG. 4 shows which of the stress levels "LEVEL A to LEVEL H" (i.e., eight levels) the person (E) is in for each of the combinations. For example, the person (E) is in the stress level of the "LEVEL C" if the autonomic balance "LF/HF" is "HIGH", the index of the parasympathetic nerve "HF" is "LOW", and the autonomic neural activity "SDNN" is "HIGH."

—CPU for Stress Determination—

The CPU for stress determination (27) reads a program from the memory for stress determination (25) and executes the program to function as a deriver (27a) and a determiner (27b) as illustrated in FIG. 2.

—Deriver—

The deriver (27a) derives multiple heartbeat-related parameters of the person (E), based on the results of the measurements by the pressure-sensitive tube (21) and the microphone (23) included in the measurer.

When extracting a heartbeat signal from a signal (a pressure signal) output from the microphone (23), the deriver (27a) obtains a variation of heartbeat intervals based on the heartbeat signal. Specifically, while the person (E) sits on the seat (G1), the deriver (27a) calculates an R wave with large amplitude, based on the heartbeat signal. The deriver (27a) obtains a length of intervals between R waves; that is of intervals between heartbeats (pulses), for each predetermined period, to calculate a periodic variation of the obtained heartbeat intervals as the variation of heartbeat intervals.

Then, the deriver (27a) obtains a standard deviation of N-N intervals (SDNN) of the person (E), using the calculated variation of heartbeat intervals. The deriver (27a) also performs a frequency analysis on the variation of heartbeat intervals to obtain (i) a ratio of a frequency component to a high frequency component (LF/HF) in the variation of heartbeat intervals, and (ii) a high frequency component "HF" in the variation of heartbeat intervals. The standard deviation of N-N intervals (SDNN), the ratio of the low frequency component to the high frequency component (LF/HF) in the variation of heartbeat intervals, and the high frequency component (HF) in the variation of heartbeat intervals are all obtained from the heartbeat intervals, and are equivalent to heartbeat-related parameters.

—Determiner—

The determiner (27b) determines a stress level of the person (E) at a current moment, using the heartbeat-related parameters derived by the deriver (27a) and the stress level determination table (26) stored in the memory for stress determination (25).

Specifically, the determiner (27b) previously obtains thresholds each corresponding to one of the three heartbeat-related parameters. The determiner (27b) compares a value of each heartbeat-related parameter derived by the deriver (27a) with a threshold corresponding to the value, and determines whether the value of each heartbeat-related parameter is below the corresponding threshold. If the value of the heartbeat-related parameter is above the threshold, the determiner (27b) determines that the parameter is "HIGH." If the value of the heartbeat-related parameter is below the threshold, the determiner (27b) determines that the parameter is "LOW." The determiner (27b) applies the determination result (i.e., "HIGH" or "LOW") of each of the heartbeat-related parameters to the stress level determination table (26) in FIG. 4, and determines the stress level of the person (E) at the current moment.

Preferably, the determiner (27b) continues operation for determining the above stress level for every predetermined time interval from immediately after the person (E) entering the space (S) sits on the chair (G) until the person (E) gets out of the space (S). Specifically, the microphone (23) periodically outputs a pressure signal generated in accordance with a level of the pressure on the pressure-sensitive tube (21) before the air conditioner (A) starts operation corresponding to a use information item until after the air conditioner (A) starts the operation (including while the operation corresponding to the use information item is being carried out and when the operation ends). Accordingly, the derivation by the deriver (27a) and the determination by the determiner (27b) are periodically carried out before the air conditioner (A) starts the operation in accordance with the use information item until after the air conditioner (A) starts the operation.

—Appliance Control Unit—

The appliance control unit (40) controls operation of at least one of the air conditioner (A), the lighting appliance (B), the acoustic appliance (C), and the aroma generation appliance (D), based on a stress level of the person (E) at a current moment determined by the stress level determination unit (20) and a use of the space (S) for the person (E). As illustrated in FIG. 2, the appliance control unit (40) includes: the touch panel (41) (equivalent to a receiver and an annunciator); a memory for appliance control (43) (equivalent to a storage unit); and a CPU for appliance control (48) (equivalent to an operation controller).

As illustrated in FIG. 1, the touch panel (41) is provided to, for example, a wall surface of the space (S). As illustrated in FIG. 2, the memory for appliance control (43) and the CPU for appliance control (48) are mounted on a printed board (P2). As illustrated in FIG. 1, the single printed board (P2) is provided in a control box near the air conditioner (A) and the aroma generation appliance (D).

Note that the printed board (P2) may be provided in the space (S).

—Touch Panel—

The touch panel (41) is removably secured to a wall surface of the space (S). Through the touch panel (41), the person (E) can enter an instruction for operation of the various appliances (A) to (D) including the air conditioner (A).

Figure 5:
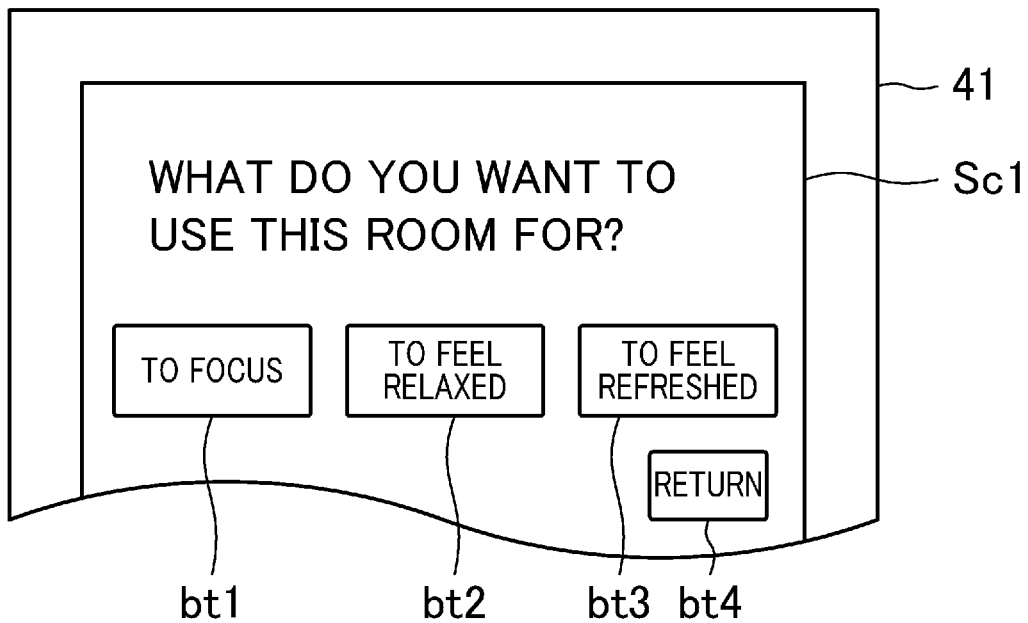
FIG. 5 is an example of a screen to be displayed on a touch panel when a person in a room enters a use of a space to be air-conditioned.

In particular, as illustrated in FIG. 5, the touch panel (41) according to this embodiment can receive, as a use information item, a use of the space (S) for the person (E). Moreover, as illustrated in FIG. 6, the touch panel (41) according to this embodiment can display, to the person (E), the stress level of the person (E) before and after such an appliance as the air conditioner (A) starts the operation in corresponding to the use information item.

FIG. 5 is an example of a screen (Sc1) to be displayed on the touch panel (41) to the person (E) when the person (E) enters the space (S). Through the screen (Sc1) in FIG. 5, the person (E) can enter his or her intended use of the space (S). This embodiment provides three different uses for the person (E); namely "TO FOCUS (to keep focusing or to focus more)", "TO FEEL RELAXED", and "TO FEEL REFRESHED." The screen (Sc) selectably displays buttons (bt1, bt2, bt3) each corresponding to one of the uses. When the person (E) selects any one of these buttons (bt1, bt2, bt3), the touch panel (41) sends the CPU for appliance control (48) data of the use corresponding to the selected button (one of bt1, bt2, bt3) as the use information item. Note that a button (bt4) representing "RETURN" is selected when the person (E) desires not to select the buttons (bt1, bt2, bt3) indicating the various objects but to see a screen other than the screen (Sc1).

Figure 6:
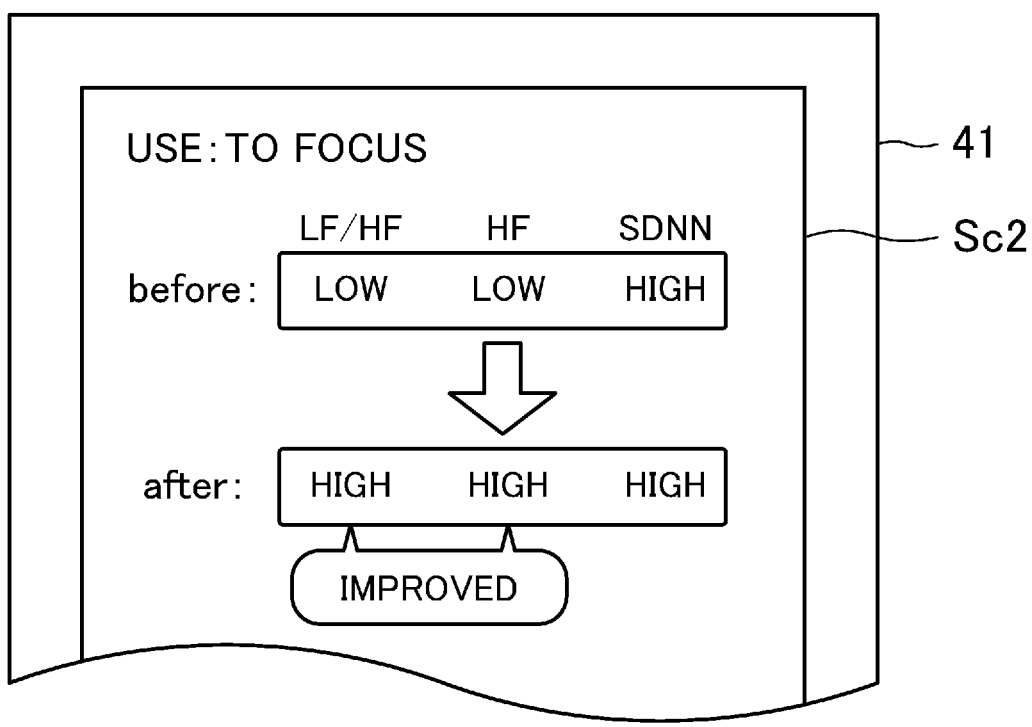
FIG. 6 is an example of a screen to be displayed on the touch panel, the screen comparably showing heartbeat-related parameters displayed when the person enters the space and heartbeat-related parameters displayed when the person leave the space.

FIG. 6 is an example of a screen (Sc2) to be displayed to the person (E) when the person (E) leaves the space (S). The screen (Sc2) is to notify the person (E) how much the stress level of the person (E) has been affected by the operation of the environment control system (10). The screen (Sc2) displays the use information item selected by the person (E). Furthermore, the screen (Sc2) comparably displays (i) values of the heartbeat-related parameters of the person (E) when the person (E) enters the space (S), and (ii) values of the heartbeat-related parameters when the person (E) leaves the space (S).

—Memory for Appliance Control—

The memory for appliance control (43) includes such a semiconductor memory as a flash memory, and such a recording medium as a hard disc. The memory for appliance control (43) stores a parameter selection table (44) (equivalent to parameter selection information) and an appliance control table (46), other than various programs to be read by the CPU for appliance control (48) so that the CPU for appliance control (48) executes various functions described below.

—Parameter Selection Table—

Described below is the parameter selection table (44) with reference to FIGS. 7 and 8. The parameter selection table (44) is used in determining which heartbeat-related parameter is to be changed (specifically to be raised) by operation of the various appliances (A) to (D) including the air conditioner (A).

As illustrated in FIG. 7, the parameter selection table (44) includes the heartbeat-related parameter, to be changed (raised) by the environment control system (10), in association with each of the use information items and the stress levels. With reference to the parameter selection table (44) in FIG. 7, if the person (E) selects a use "to focus" and the stress level determination unit (20) shows the "level A" as a determination result (a stress level of the person (E)) observed when the use is entered, the heartbeat-related parameter to be changed is the "LF/HF."

The parameter selection table (44) in FIG. 7 is created in accordance with a table (45) in FIG. 8 indicating priorities of the heartbeat-related parameters. FIG. 8 shows that the heartbeat-related parameters have priorities previously set for each of the use information items. Specifically, FIG. 8 shows that the priorities are given to different heartbeat-related parameters to be raised, depending on the use for the person (E).

For example, if the use information item is "TO FOCUS", the ratio of the low frequency component to the high frequency component in the variation of heartbeat intervals "LF/HF" needs to be raised by the highest priority, and the high frequency component in the variation of heartbeat intervals "HF" has the second highest priority. The standard deviation of N-N intervals "SDNN" has the lowest priority. This is because when the person (E) desires to focus a higher priority needs to be given to the low frequency component "LF" that is the index of the sympathetic nerve than to the high frequency component "HF" that is the index of the parasympathetic nerve. That is why the highest priority is given to the ratio of the low frequency component to the high frequency component "LF/HF." Moreover, when the person (E) tries to focus, the "HF" that relates to the "LF/HF" needs to be raised instead of the autonomic neural activity "SDNN." That is why the autonomic neural activity "SDNN" has the lowest priority. The priorities of the heartbeat-related parameters for uses "TO FEEL RELAXED" and "TO FEEL REFRESHED" other than "TO FOCUS" are also determined in a similar manner.

Then, other than the priorities corresponding to the use information items (FIG. 8), the heartbeat-related parameter to be changed in the parameter selection table (44) in FIG. 7 is determined in accordance with a stress level defined by a magnitude relationship between the heartbeat-related parameters and the corresponding thresholds.

Specifically, in FIG. 4, if the person (E) is in the stress level in which the heartbeat-related parameters below the thresholds are not found (LEVEL A), the heartbeat-related parameter having the highest priority in FIG. 8 is assigned in FIG. 7 as a heartbeat-related parameter to be raised. Hence, in the record having the stress level "level A" in FIG. 7, the "LF/HF" is assigned for the use information item "to focus", the "HF" is assigned for the use information item "to feel relaxed", and the "SDNN" is assigned for the use information item "to feel refreshed."

Specifically, in FIG. 4, if the person (E) is in a stress level (one of LEVELs B, C, E) in which one of the heartbeat-related parameters is below a corresponding one of the thresholds, the one heartbeat-related parameter below the threshold or the heartbeat-related parameter having the highest priority in FIG. 8 is assigned in FIG. 7 as a heartbeat-related parameter to be raised. For example, FIG. 4 clearly shows that, in the stress level "LEVEL B", both the "LF/HF" and the "HF" are "HIGH", but only the "SDNN" is below the threshold and "LOW." Hence, the heartbeat-related parameter "SDNN" below the threshold is assigned to the record of the "LEVEL B" in FIG. 7, regardless of the kinds of the use information items. Moreover, FIG. 4 clearly shows that, in the stress level "LEVEL E", the "LF/HF" is the only heartbeat-related parameter below the threshold. However, FIG. 8 shows that, for the use information item "TO FOCUS", the heartbeat-related parameter "LF/HF" has the highest priority, but does not have the highest priority in other use information items "TO FEEL RELAXED" and "TO FEEL REFRESHED." Hence, in the record of the stress level "LEVEL E" in FIG. 7, if the use information item is "TO FOCUS", the "LF/HF" is assigned; whereas, the heartbeat-related parameter "HF" having the highest priority in FIG. 8 is assigned if the use information item is "TO FEEL RELAXED", and the heartbeat-related parameter "SDNN" having the highest priority in FIG. 8 is assigned if the use information item is "TO FEEL REFRESHED."

Specifically, in FIG. 4, if the person (E) is in a stress level (one of LEVELs D, F, G, I) in which two or more of the heartbeat-related parameters are below respective thresholds, the heartbeat-related parameter having the highest priority of all the heartbeat-related parameters below the thresholds is assigned in FIG. 7 as a heartbeat-related parameter to be raised. FIG. 4 clearly shows that, in the stress level "LEVEL D", for example, the heartbeat-related parameters "HF" and "SDNN" are below the respective thresholds. Here, in accordance with the priority for each of the use information items in FIG. 8, either the "HF" or the "SDNN" having a higher priority is assigned as the heartbeat-related parameter to be raised for the use information items in the stress level "LEVEL D" in FIG. 7. Specifically, in the stress level "LEVEL D" in FIG. 7, the "HF" is assigned if the use information item is either "TO FOCUS" or "TO FEEL RELAXED" and the "SDNN" is assigned if the use information item is "TO FEEL REFRESHED."

—Appliance Control Table—

Described next is the appliance control table (46) with reference to FIG. 9. The appliance control table (46) is used in determining how to operate the various appliances (A) to (D) when a heartbeat-related parameter is to be changed (specifically to be raised).

As illustrated in the appliance control table (46) of FIG. 9, season, kind of a heartbeat-related parameter to be raised, set temperature of the air conditioner (A), illuminance of the lighting appliance (B), sound to be output from the acoustic appliance (C) and aroma to be released from the aroma generation appliance (D) are associated with one another. A set temperature of the air conditioner (A), an illuminance of the lighting appliance (B), a sound to be output by the acoustic appliance (C), and an aroma to be released by the aroma generation appliance (D) are appropriately determined, depending on heartbeat-related parameters and a season, to affect a stress level of the person (E) so that the stress level is changed to conform to the use of the space (S).

For example, if the season is "SUMMER", different set temperatures, illuminances, sounds, and aromas are set for different heartbeat-related parameters to be raised. If the season is "WINTER", again, different set temperatures are set for different heartbeat-related parameters. Note in FIG. 9 that a set temperature in the season "WINTER" is different from that in the season "SUMMER"; whereas, an illuminance, a sound, and an aroma are the same in the seasons "WINTER" and "SUMMER."

In FIG. 9, as an example, regardless of the seasons, the set temperature is (i) the lowest if the heartbeat-related parameter to be raised is the "LF/HF" of all the three heartbeat-related parameters, and (ii) the highest if the heartbeat-related parameter to be raised is the "SDNN" of all the three heartbeat-related parameters. Moreover, in FIG. 9, the illuminance of the lighting appliance (B) is represented in kind of color (whitish color and warm color), color temperature (k), and rated luminous flux (lm). The sound to be output by the acoustic appliance (C) is represented in tone (sounds of a string instrument and a piano) and sound in nature (sounds of a rushing creak and rain) effective to raise the heartbeat-related parameters. The aroma to be released by the aroma generation appliance (D) is represented in kind of aroma (herbs, trees, and flowers) effective to raise the heartbeat-related parameters.

Note that the appliance control table (46) illustrated in FIG. 9 is merely an example, and the operation of the various appliances (A) to (D) shall not be limited to the one described in FIG. 9.

—CPU for Appliance Control—

The CPU for appliance control (48) reads a program from the memory for appliance control (43) and executes the program to function as a touch panel controller (48a), a mode determiner (48b), an air-conditioning controller (48c), and an appliance controller (48d) as illustrated in FIG. 2.

—Touch Panel Controller—

The touch panel controller (48a) provides the touch panel (41) with information on the screens (Sc1, Sc2), and analyzes the information entered by the person (E) and received by the touch panel (41). The entered information includes the above use information items.

—Mode Determiner—

The mode determiner (48b) determines in which mode the various appliances (A) to (D) including the air conditioner (A) operate, depending on a use information item from the touch panel (41). Examples of kinds of the modes according to this embodiment include a "FOCUS MODE", a "RELAXING MODE", and a "REFRESHING MODE" for the respective use information items.

—Air-Conditioning Controller—

The air-conditioning controller (48c) controls the operation of the air conditioner (A). In particular, the air-conditioning controller (48c) selects a heartbeat-related parameter to be changed from among the heartbeat-related parameters (the "LF/HF", the "HF", the "SDNN") depending on the person (E)'s current stress level output by the stress level determination unit (20) and a mode determined in accordance with a use information item, and controls the operation of the air conditioner (A) so that the selected heartbeat-related parameter is to be changed (specifically to be raised).

Specifically, the air-conditioning controller (48c) applies the current stress level and the mode determined in accordance with the use information item to the parameter selection table (44) in FIG. 7, and selects a heartbeat-related parameter to be changed (raised).

As already described, the parameter selection table (44) in FIG. 7 is set by the priorities of the heartbeat-related parameters according to FIG. 8. Hence, the air-conditioning controller (48c) is to select a heartbeat-related parameter to be changed (raised), in accordance with priority orders, of the heartbeat-related parameters, corresponding to a use information item received by the touch panel (41) and a result of the determination (i.e., a stress level) by the determiner (27b).

Next, the air-conditioning controller (48c) applies the current season and the selected heartbeat-related parameter to the parameter selection table (46) in FIG. 9 to determine the set temperature of the air conditioner (A). Then, the air-conditioning controller (48c) causes the air conditioner (A) to adjust the temperature in the space (S) to the set temperature.

Thanks to such operation control by the air-conditioning controller (48c), the air conditioner (A) operates to raise the heartbeat-related parameter having the highest priority when the person (E) is in a stress level in the heartbeat-related parameters below the thresholds are not found. If the person (E) is in a stress level in which one of the heartbeat-related parameters below the thresholds, the air conditioner (A) operates to raise either the one heartbeat-related parameter below the threshold or the heartbeat-related parameter having the highest priority. If the person (E) is in a stress level in which two or more heartbeat-related parameters are below respective thresholds, the air conditioner (A) operates to raise the heartbeat-related parameter having the highest priority of all the heartbeat-related parameters.

As described before, the stress level determination unit (20) continues to output the latest stress level of the person (E) for every predetermined time interval while the air conditioner (A) is operating depending on the use information item. Hence, depending on a use information item already received by the touch panel (41) and a stress level of the person (E) observed while the air conditioner (A) is operating for the use information item, the air-conditioning controller (48c) preferably reselects a heartbeat-related parameter from the parameter selection table (44) in FIG. 7 and applies the reselected heartbeat-related parameter to the appliance control table (46) in FIG. 9 to reset the set temperature of the air conditioner (A). Specifically, the air-conditioning controller (48c) preferably feedback-controls the air conditioner (A), depending on the person (E)'s latest stress level to be sent periodically.

—Appliance Controller—

The appliance controller (48d) controls operation of the appliances (B) to (D) other than the air conditioner (A). Note that the appliance controller (48d) is different only as to the appliances to control from the above air-conditioning controller (48c). The appliance controller (48d) is similar in details of the control to the above air-conditioning controller (48c).

Specifically, the appliance controller (48d) selects a heartbeat-related parameter using the parameter selection table (44) in FIG. 7, and applies the selected heartbeat-related parameter to the appliance control table (46) in FIG. 9 to determine at least one of the illuminance of the lighting appliance (B), the sound to be output by the acoustic appliance (C), and the aroma to be released by the aroma generation appliance (D). In accordance with the determination, the appliance controller (48d) causes the appliances (B) to (D) other than the air conditioner (A), to change (raise) the selected heartbeat-related parameter. Moreover, the appliance controller (48d) preferably feedback-controls the appliances (B) to (D) other than the air conditioner (A), depending on the person (E)'s latest stress level to be sent periodically.

Hence, the environment control system (10) according to this embodiment controls operation of both the air conditioner (A) and the appliances (B) to (D) other than the air conditioner (A) to cause the air conditioner (A) and the appliances (B) to (D) to affect the change of the selected heartbeat-related parameter. Thus, compared with the case where the operation of the air conditioner (A) alone is controlled, the stress level of the person (E) conforms more exactly to a use of the space (S).

<Operation of Environment Control System>

Briefly described below is a sequence of operation performed by the air-conditioning control system (10), with reference to FIG. 10.

When a person (the person (E)) enters the space (S), first, the touch panel controller (48a) of the appliance control unit (40) causes the touch panel (41) to display the screen (Sc1) of FIG. 5 to obtain a use of the space (S) for the person (Step St1).

If the person (the person (E)) entering the space (S) selects any one of buttons (bt1 to bt3) on the screen (Sc1) in FIG. 5 of the touch panel (41) (Yes at Step St2), the touch panel (41) sends the CPU for appliance control (48) the selection as a use information item. If the person (E) does not select any one of the buttons (bt1 to bt3) (No at Step St2), the screen (Sc1) in FIG. 5 is left displayed on the touch panel (41). If the person (E) selects a button "RETURN" (bt4) from the screen (Sc1) in FIG. 5, the touch panel (41) switches displaying screens from the screen (Sc1) in FIG. 5 to another screen (e.g., a normal screen), and the environment control system (10) does not proceed to the sequence of operation described below.

In Step St2, the CPU for appliance control (48) obtains the use information item (Yes at Step St2), and then the pressure-sensitive tube (21) receives pressure while the person (E) is sitting on the chair (G). If the microphone (23) outputs a pressure signal depending on the pressure, the CPU for stress determination (27) can determine that the person (E) is sitting (Yes at Step St3). Here, the deriver (27a) derives a heartbeat-related parameter (L/F, HF, SDNN) of the person (E) at a current moment based on the pressure signal, and the determiner (27b) determines the current stress level of the person (E), using the derived heartbeat-related parameter in FIG. 4 and the stress level determination table (26) (Step St4).

The mode determiner (48b) of the CPU for appliance control (48) determines, from the use information item, a mode in which appliances such as the air conditioner (A) are to operate. Using the determined mode, the current stress level of the person (E), and the parameter selection table (44) in FIG. 7, the air-conditioning controller (48c) and the appliance controller (48d) select a heartbeat-related parameter to be changed (raised) (Step St5).

Using the selected heartbeat-related parameter and the appliance control table (46) in FIG. 9, the air-conditioning controller (48c) and the appliance controller (48d) determine such factors as a set temperature and an illuminance. The air-conditioning controller (48c) causes the air conditioner (A) to adjust the temperature in the space (S) to the determined set temperature. The appliance controller (48d) operates the appliances (B) to (D) in accordance with the determined factors such as the illuminance of the lighting appliance (B), the sound to be output by the acoustic appliance (C), and the aroma to be released by the aroma generation appliance (D) (Step St6).

The environment control system (10) repeats the operation Step St4 through Step St6 every time a predetermined time period elapses from Step St6 (Yes at Step St7).

Even though the predetermined time period has not elapsed from Step St6 (No at Step St7), if the appliance control unit (40) obtains information indicating that the person (E) enters "LEAVING" through, for example, the touch panel (41) and leaves the space (S) (Yes at Step St8), the deriver (27a) of the stress level determination unit (20) derives a heartbeat-related parameter (i.e., the latest heartbeat-related parameter) of the person (E) at a current moment based on a pressure signal currently output by the microphone (23) (Step St9).

The touch panel controller (48a) generates data of the screen (Sc2) for displaying on a single screen the heartbeat-related parameter derived at the beginning of the sequence of the operation and the latest heartbeat-related parameter derived at Step St9. Then, the touch panel controller (48a) outputs the generated data to the touch panel (41). Hence, the touch panel (41) displays the screen (Sc2) for the person (E) to identify how much the heartbeat-related parameter of the person (E) has changed before and after the sequence of the operation of the appliances (A) to (D) performed depending on the use for, and the stress level of, the person (E) (Step St10).

<Effects>

In this embodiment, a stress level of the person (E) at a current moment is determined, based on a heartbeat-related parameter of the person (E). Then, depending on the determined stress level and a use of the space (S) for the person (E), a heartbeat-related parameter to be changed is selected from among multiple heartbeat-related parameters. Operation of the air conditioner (A) is controlled to change the selected heartbeat-related parameter. For example, the use for the person (E) is "TO FOCUS." If the person (E) has already been in the strained state, the environment control system (10) operates the air conditioner (A) so that the strained state of the person (E) continues longer, instead of making the person (E) feel relaxed. Moreover, if the person (E) is in the fatigued state, the environment control system (10) causes the air conditioner (A) to operate so that the person (E) is guided to feel strained, instead of being guided to feel relaxed. Hence, the environment control system (10) provides the space (S) with an environment for guiding the person (E) to a stress level which conforms to a use of the space (S). Thus, the person (E) can change or maintain his or her stress level, and efficiently use, the space (S) depending on the use of the space (S).

Moreover, in this embodiment, priorities to be selected are preset to the heartbeat-related parameters for each of the use information items, as shown in FIG. 8. The CPU for appliance control (48) selects a heartbeat-related parameter to be changed, depending on the priorities corresponding to a use (a use information item) for the person (E) and a stress level of the person (E). Specifically, the heartbeat-related parameter to be changed is selected not at random but as appropriate to suit the use for the person (E). Thus, the stress level of the person (E) can be adjusted to suit the use more exactly so that the person (E) can achieve the purpose of the use more easily.

As illustrated in FIG. 7, the parameter selection table (44) of this embodiment, stored in the memory for appliance control (43), includes the heartbeat-related parameter to be changed in association with each of the use information items and stress levels. Using the parameter selection table (44), the CPU for appliance control (48) can easily and quickly determine a heartbeat-related parameter to be changed for achieving the purpose of use for the person (E), without determining the priorities in FIG. 8 every time. Such a feature facilitates processing for selection of the heartbeat-related parameter, reducing the time period required for the processing.

Specifically, in FIG. 7 according to this embodiment, if the person (E) is in a stress level in which the heartbeat-related parameters below the thresholds are not found, the heartbeat-related parameter having the highest priority is to be raised. Hence, the current heartbeat-related parameters are to be maintained. If the person (E) is in a stress level in which one of the heartbeat-related parameters is below a corresponding one of the thresholds, and the one heartbeat-related parameter below the threshold is raised, the parameter is needed to achieve the purpose of use, and therefore is to be raised. Moreover, if the person (E) is in a stress level in which one of the heartbeat-related parameters is below the corresponding threshold and the one heartbeat-related parameter below the threshold is not related to the use, the heartbeat-related parameter having the highest priority is to be raised. If the person (E) is in a stress level in which two or more of the heartbeat-related parameters are below respective thresholds, the heartbeat-related parameter having the highest priority is to be raised for achieving the purpose of use.

Hence, the environment control system (10) can reliably select a heartbeat-related parameter to be raised, depending on the presence or absence of a heartbeat-related parameter below the corresponding threshold and the number of heartbeat-related parameters below respective thresholds, contributing to providing an environment in which a stress level of the person (E) conforms to a use of the space (S).

Moreover, the heartbeat-related parameters according to this embodiment include the standard deviation of N-N intervals (SDNN) of the person (E), the ratio of the low frequency component to the high frequency component (LF/HF) in the variation of the N-N intervals, and the high frequency component (HF) in the variation of the N-N intervals. If a use information item indicates maintenance of or improvement in a focused state of the person (E), the priorities are set in the order of the ratio of the low frequency component to the high frequency component (LF/HF) in the variation of N-N intervals, the high frequency component (HF) in the variation of N-N intervals, and the standard deviation of N-N intervals (SDNN). Such a feature makes the space (S) appropriate for the use; namely, maintaining or improving the focused state of the person (E).

In this embodiment, a heartbeat-related parameter to be changed is reselected depending on a stress level of the person (E) during the operation of the air conditioner (A) and the use information item, and the operation of the air conditioner (A) is feedback-controlled to change the selected heartbeat-related parameter. Such a feature allows the environment control system (10) to provide the space (S) with an environment which precisely suits stress levels of the person (E) at different times.

In this embodiment, the touch panel (41) displays the screen (Sc2) illustrated in FIG. 6. This screen (Sc2) allows the person (E) to identify how much the heartbeat-related parameter of the person (E) himself or herself has changed before and after the start of the operation of the air conditioner (A) for the use.

In this embodiment, operation of at least one of the lighting appliance (B), the acoustic appliance (C), and the aroma generation appliance (D) other than the air conditioner (A) is controlled to change a selected heartbeat-related parameter. Such a feature allows the environment control system (10) to provide an environment in which the heartbeat-related parameter changes more easily in conformity with a use for the person (E) than when the air conditioner (A) alone operates.

Other Embodiments

The above embodiment may also be configured as follows.

Any given parameter can be a heartbeat-related parameter related to heartbeat intervals as long as the parameter is an index for obtaining a stress level of the person (E). Hence, multiple heartbeat-related parameters may include other indexes than the "LF/HF", the "HF", and the "SDNN". A combination of the heartbeat-related parameters does not have to include the "LF/HF", the "HF", and the "SDNN."

The above embodiment describes the case where a priority is set to each of the heartbeat-related parameters when the heartbeat-related parameter is selected. However, the priority does not necessarily have to be set.

The memory for appliance control (43) may include the table (45) in FIG. 8, instead of the parameter selection table (44) in FIG. 7. In this case, the CPU for appliance control (48) may apply a use information item to the table (45) in FIG. 8 and determine whether a value of each heartbeat-related parameter derived is below the threshold, before selecting a heartbeat-related parameter to be changed.

In the above embodiment, the environment control system (10) performs the actions (I) to (III) below.

(I) If the person (E) is in a stress level in which the heartbeat-related parameters below the thresholds are not found, the environment control system (10) causes the air conditioner (A) to raise the heartbeat-related parameter having the highest priority.

(II) If the person (E) is in a stress level in which one of the heartbeat-related parameters is below a corresponding one of the thresholds, the environment control system (10) operates the air conditioner (A) to raise either the one heartbeat-related parameter below the corresponding threshold or the heartbeat-related parameter having the highest priority.

(III) If the person (E) is in a stress level in which two or more of the heartbeat-related parameters below respective thresholds, the environment control system (10) causes the air conditioner (A) to raise the heartbeat-related parameter having the highest priority of all the two or more of the heartbeat-related parameters below the respective thresholds.

However, the technique to select a heartbeat-related parameter to be changed does not have to be limited to the above actions (I) to (III) themselves.

The thresholds of the heartbeat-related parameters to be used for determination of a stress level may vary, depending on at least either the age or the sex of the person (E).

The use information items shall not be limited to "TO FOCUS", "TO FEEL RELAXED", and "TO FEEL REFRESHED." Moreover, priorities of the heartbeat-related parameters in each of the use information items shall not be limited to those in FIG. 8.

The various appliances (A) to (D) do not have to be feedback-controlled while performing operation in accordance with a use information item.

The operation to determine a stress level may be performed at least immediately before the air conditioner (A) starts operation in accordance with the use for the person (E). The determination operation does not necessarily have to be performed during the operation of the air conditioner (A) and immediately before the person (E) leaves the space (S).

The techniques to receive a use information item and to announce a stress level before and after the operation corresponding to the use information item shall not be limited to displaying the information and the stress level on a screen of the touch panel (41). An example of the technique to receive a use information item may be voice input, and examples of the techniques to announce a stress level may be voice output alone, and a combination of display and voice output. Note that it is not necessary to have a technique to leave the stress level as it is.

It is necessary to have the air conditioner (A) as an appliance to operate in accordance with a use information item; however, it is not necessary to have the lighting appliance (B), the acoustic appliance (C), and the aroma generation appliance (D). At least one of the appliances (B) to (D) may be the one to operate in accordance with a use information item. Furthermore, an appliance other than the appliances (B) to (D) may be the one to operate or included in the appliances.

The order of Steps St2 to St4 in FIG. 10 shall not be limited to the one in FIG. 10. For example, the steps may be carried out in the order of Steps St3, St4, and St2.

In principle, a value of a selected heartbeat-related parameter is controlled to rise; however, the value may be controlled to fall in certain instances.

INDUSTRIAL APPLICABILITY

As can be seen, the present invention is useful for a system to provide an appropriate environment in accordance with a stress level of a person in a room and a use of a space in which the person stays.

DESCRIPTION OF REFERENCE CHARACTERS

10 Environment Control System (Air-Conditioning Control System)
21 Pressure-Sensitive Tube (Measurer)
23 Microphone (Measurer)
27a Deriver
27b Determiner
41 Touch Panel (Receiver and Annunciator)
43 Memory for Appliance Control (Storage Unit)
44 Parameter Selection Table (Parameter Selection Information)
48 CPU for Appliance Control (Operation Controller)
A Air Conditioner
B Lighting Appliance
C Acoustic Appliance
D Aroma Generation Appliance

The invention claimed is:

1. An air-conditioning control system comprising:
a measurer measuring a body movement of a person in a room, a space of which is to be air-conditioned by an air conditioner;
a deriver deriving heartbeat-related parameters based on a result of the measurement by the measurer, the heartbeat-related parameters being related to N-N intervals of the person;
a determiner determining a stress level of the person at a current moment based on the heartbeat-related parameters;
a receiver capable of receiving a use information item indicating a use of the space for the person; and
an operation controller (i) selecting a heartbeat-related parameter to be changed from among the heartbeat-related parameters depending on a result of the determination by the determiner and the use information item, and (ii) controlling operation of the air conditioner to change the selected heartbeat-related parameter to be changed, wherein
the heartbeat-related parameters have priorities previously set for each of the use information items, the priorities being unchangeable and applicable when the heartbeat-related parameters are to be selected to be changed,
the operation controller selects the heartbeat-related parameter to be changed, depending on the priorities corresponding to the received use information item, and the result of the determination by the determiner,
the determiner compares the heartbeat-related parameters with thresholds each corresponding to one of the heartbeat-related parameters to determine the stress level of the person,
for each of a plurality of stress levels, the heartbeat-related parameter to be changed for each of a plurality of use information items is set as follows:
if none of the heartbeat-related parameters are below the thresholds, the heartbeat-related parameter included in the heartbeat-related parameters having a highest priority among the priorities is set as the heartbeat-related parameter to be changed;
if one of the heartbeat-related parameters is below a corresponding one of the thresholds, either the one heartbeat-related parameter below the threshold or the heartbeat-related parameter having the highest priority is set as the heartbeat-related parameter to be changed; and
if two or more of the heartbeat-related parameters are below respective thresholds among the thresholds, the heartbeat-related parameter having the highest priority among the two or more of the heartbeat-related parameters is set as the heartbeat-related parameter to be changed.

2. The air-conditioning control system of claim 1 further comprising
a storage unit storing a parameter selection information table indicating the heartbeat-related parameter to be changed in association with each of a plurality of stress levels and each of a plurality of use information items, wherein
the determiner compares the heartbeat-related parameters with thresholds each corresponding to one of the heartbeat-related parameters to determine the current stress level of the person from the plurality of stress levels,
in the parameter selection information table, the heartbeat-related parameter to be changed is determined in accordance with the priorities for each of the use information items and a magnitude relationship between the heartbeat-related parameters and the corresponding thresholds, and
the operation controller selects the heartbeat-related parameter to be selected, using the parameter selection information table.

3. The air-conditioning control system of claim 1, wherein
the heartbeat-related parameters include a standard deviation of N-N intervals (SDNN) of the person, a ratio of a low frequency component to a high frequency component (LF/HF) in a variation of the N-N intervals, and a high frequency component (HF) in the variation of the N-N intervals, and
if the use information item indicates maintenance of or improvement in a focused state of the person, the priorities are set in an order of the ratio of the low frequency component to the high frequency component (LF/HF) in the variation of the N-N intervals, the high frequency component (HF) in the variation of the N-N intervals, and the standard deviation of the N-N intervals (SDNN).

4. The air-conditioning control system of claim 1, wherein
the measurer measures the body movement of the person during the operation of the air conditioner,
the deriver derives the heartbeat-related parameters of the person during the operation of the air conditioner,
the determiner determines the stress level of the person during the operation of the air conditioner, and
the operation controller reselects the heartbeat-related parameter to be changed depending on the stress level of the person during the operation of the air conditioner and the use information item, and feedback-controls the operation of the air conditioner so that the reselected heartbeat-related parameter changes.

5. The air-conditioning control system of claim 1, wherein
the measurement by the measurer, the derivation by the deriver, and the determination by the determiner are carried out at least before and after the air conditioner starts the operation corresponding to the use information item, the air-conditioning control system further comprising an annunciator announcing to the person the stress level before and after the air conditioner starts the operation corresponding to the use information item.

6. The air-conditioning control system of claim 1 further comprising
at least one of a lighting appliance, an acoustic appliance, and an aroma generation appliance all of which correspond to the space, wherein
the operation controller further controls operation of at least one of the lighting appliance, the acoustic appliance, and the aroma generation appliance to change the selected heartbeat-related parameter to be changed.

* * * * *